United States Patent
Fina

(10) Patent No.: US 6,248,113 B1
(45) Date of Patent: Jun. 19, 2001

(54) DEVICE FOR THE ELECTROLYTIC DISSOLUTION OF URINARY STONES AND RELATED METHOD OF TREATMENT OF URINARY CALCULOSIS

(76) Inventor: Ernesto Fina, Viale Villa Maio, 10, Napoli (IT)

( * ) Notice: Subject to any disclaimer, the term of this patent is extended or adjusted under 35 U.S.C. 154(b) by 0 days.

(21) Appl. No.: 09/261,189

(22) Filed: Mar. 3, 1999

Related U.S. Application Data

(63) Continuation-in-part of application No. 08/876,315, filed on Jun. 16, 1997, now abandoned.

(30) Foreign Application Priority Data

Jun. 20, 1996 (IT) .............................................. NA960049 U

(51) Int. Cl.[7] .................................................. A61B 17/22
(52) U.S. Cl. ............................ 606/127; 606/128; 606/2.5
(58) Field of Search .............................. 606/127, 2.5, 49, 606/128

(56) References Cited

U.S. PATENT DOCUMENTS

| | | | |
|---|---|---|---|
| 3,792,701 | * | 2/1974 | Kloz et al. .............................. 606/2.5 |
| 3,941,122 | * | 3/1976 | Jones ..................................... 606/128 |
| 4,190,051 | * | 2/1980 | Iglesias ................................. 606/128 |
| 4,192,294 | * | 3/1980 | Vasilevsky et al. ................... 606/128 |
| 4,589,415 | * | 5/1986 | Haaga ................................... 606/127 |
| 4,611,594 | * | 9/1986 | Grayhack et al. ......................... 601/4 |
| 4,691,706 | * | 9/1987 | Takayama .............................. 606/127 |
| 4,768,505 | * | 9/1988 | Okada et al. .............................. 601/4 |
| 4,966,132 | * | 10/1990 | Nowacki et al. ....................... 128/24 |
| 4,997,435 | * | 3/1991 | Demeter ................................ 606/127 |
| 5,152,767 | * | 10/1992 | Sypal et al. ........................... 606/128 |
| 5,195,508 | * | 3/1993 | Muller et al. ........................... 128/24 |
| 5,239,985 | * | 8/1993 | Muniz et al. ........................... 128/24 |
| 5,254,121 | * | 10/1993 | Manevitz et al. ..................... 606/128 |
| 5,496,330 | * | 3/1996 | Bates et al. ........................... 606/127 |
| 5,741,272 | * | 4/1998 | Kuhne .................................. 606/128 |
| 5,860,972 | * | 1/1999 | Kloz et al. ............................. 606/2.5 |

* cited by examiner

*Primary Examiner*—Gene Mancene
*Assistant Examiner*—Michael B. Priddy
(74) *Attorney, Agent, or Firm*—Guido Modiano; Albert Josif; Daniel O'Byrne

(57) ABSTRACT

A device for the electrolytic dissolution of urinary calculi in patients affected by urinary calculosis, the particularity whereof consists of the fact that it has: a tubular sleeve which is meant to be inserted in the urinary cavities of a patient, a cathode electrode accommodated in the sleeve, and at least one anode electrode which can slide within the sleeve so as to protrude, in an active position, from the sleeve in order to make contact with a calculus and dissolve it electrolytically in association with the cathode electrode.

22 Claims, 3 Drawing Sheets

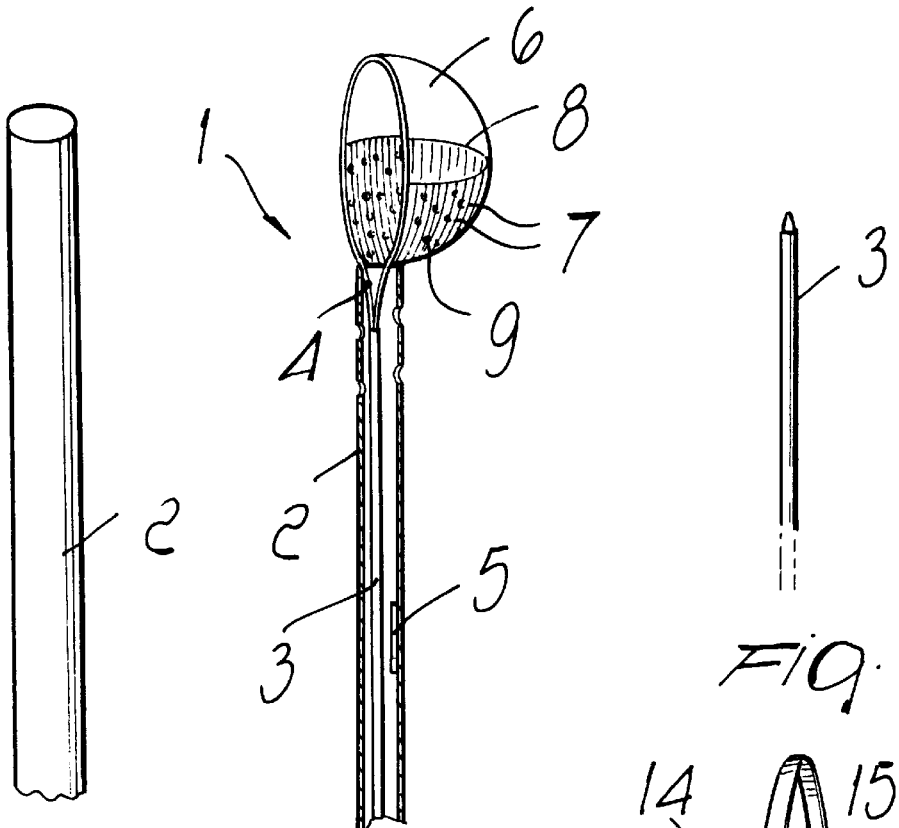
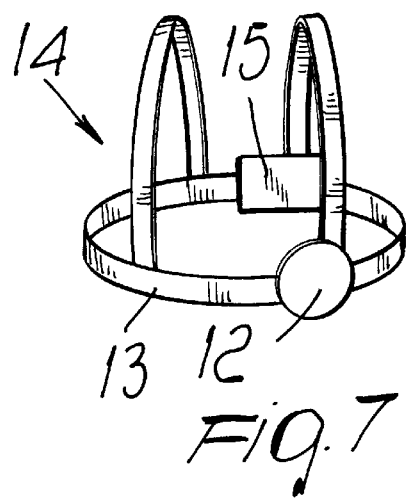
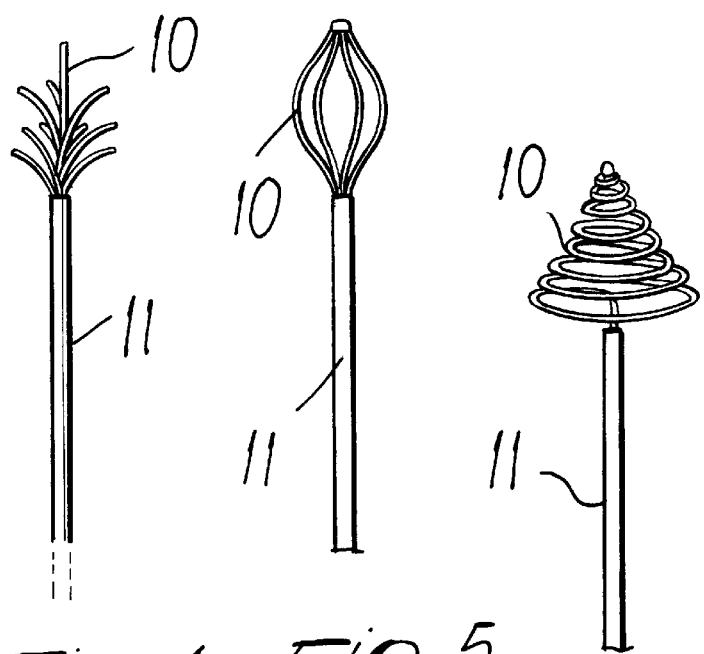
Fig.1  Fig.2  Fig.3  Fig.7  Fig.4  Fig.5  Fig.6

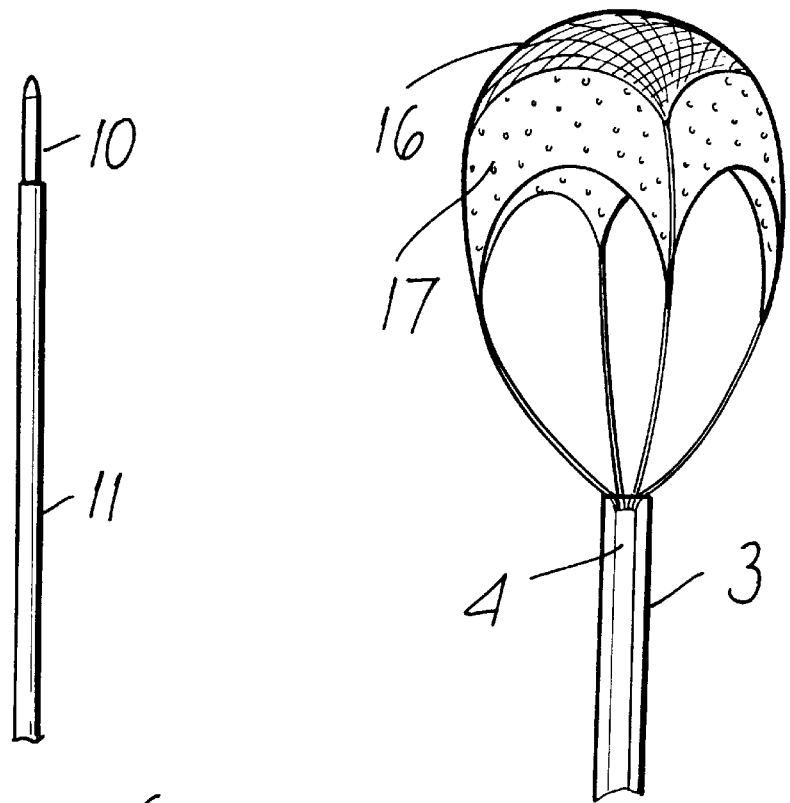
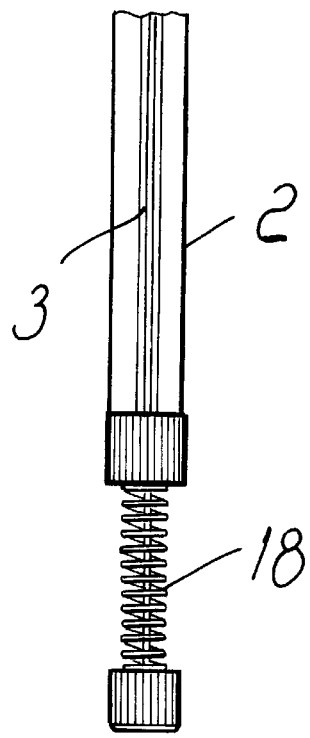

DEVICE FOR THE ELECTROLYTIC DISSOLUTION OF URINARY STONES AND RELATED METHOD OF TREATMENT OF URINARY CALCULOSIS

CROSS-REFERENCE TO RELATED APPLICATIONS

This application is a continuation-in-part of application Ser. No. 08/876,315, filed on Jun. 16, 1997, now abandoned.

BACKGROUND OF THE INVENTION

1. Field of the Invention

The present invention relates to a device for the electrolytic dissolution of urinary calculi and to the related method of treatment of urinary calculosis.

In particular, the present invention relates to a device which is capable of producing the electrolytic dissolution of urinary calculi, or electrolitholysis, in the urinary tract without having to resort to hospitalization of the patient.

2. Prior Art

The treatment of urinary calculosis is the subject of intense research both in the pharmacological and in the surgical field.

In the treatment of urinary calculosis, attempts have always been made to achieve dissolution of calculi rather than fragmentation, since fragmentation, even if achieved in an optimum manner, entails a high risk of retaining in the urinary cavities fragments which can constitute a nucleus for the formation of new calculi.

Dissolution of calculi by chemical means, or chemolitholysis, entails the perfusion of solutions, formulated appropriately according to the composition of the calculus to be treated, along the urinary tract proximate to the body region where the calculus is located.

In performing chemolitholysis, appropriately shaped tubes are inserted endoscopically or percutaneously and then a solution that contains active principles, selected appropriately according to the composition of the calculus to be dissolved, is perfused.

The chemical dissolution method, however, has not yielded satisfactory results, since it requires long treatment times which make it poorly tolerated by patients. The person subjected to the treatment furthermore complains of pains and burning sensations due to the damaging and irritating action which the perfused pharmacological solutions induce at the level of the epithelium that lines the urinary tract.

In the field of the fragmentation of calculi by applying energy in the form of shock waves, ultrasound or electrohydraulic waves, many methods and devices have been recently devised and improved which have allowed to break up a calculus both from outside the human body (extracorporeal shock wave lithotripsy or ESWL) and by introducing operating instruments percutaneously or endoscopically in the urinary cavities (PCNL and URSL).

These recent methods, however, are not free from drawbacks, which are mainly due to imperfect fragmentation of the calculus, consequently forming fragments which inside a renal calyx can constitute a nucleus for the precipitation and aggregation of crystals, causing regrowth of the calculus and relapse of the lithiasic disorder a short time after. These drawbacks occur mostly after extracorporeal treatments.

Moreover, some calculi which have a particular chemical composition, such as for example cystine and calcium oxalate monohydrate calculi, are particularly resistant to the action of shock waves and in the best of cases can be fragmented only into large fragments which are impossible to expel.

The need is therefore currently felt, in the field of microinvasive surgery, to have methods and devices which lead to complete freedom from calculi (calculus-free status) without the need for hospitalization and anaesthesia.

SUMMARY OF THE INVENTION

An aim of the present invention is to provide a device for the electrolytic dissolution of urinary calculi to be applied to out-patients affected by urinary calculi without resorting to general or regional anaesthesia of the patient.

An object of the present invention is to provide a device for the electrolytic dissolution of urinary calculi which is compact, easy to apply by urologists and well-tolerated by patients.

Another object of the invention is to provide a method for the electrolytic dissolution of renal calculi which provides effective dissolution of renal calculi without residual stones as after treatments of stone fragmentation.

Another object of the present invention is to provide a device for the electrolytic dissolution of calculi which is highly reliable and relatively easy to manufacture at competitive costs.

In accordance with one preferred aspect of the invention, there is provided a device for the dissolution of urinary calculi in patients affected by urinary calculosis, which includes:

- a tubular sleeve adapted for insertion in a urinary cavity of a patient; and
- a pair of electrodes connectable to a source of electricity so as to form an electrolytic circuit for electrolytic calculus dissolution;
- wherein at least one of the pair of electrodes is slidably accommodated inside the tubular sleeve between:
  - a first position in which the slidable electrode is substantially completely accommodated inside the tubular sleeve for facilitating the insertion of the electrode inside the urinary cavity of the patient; and
  - a second position in which the slidable electrode protrudes outside of the tubular sleeve once the tubular sleeve has been inserted inside the urinary cavity of the patient for making contact with a calculus located in the urinary cavity of the patient for electrolytic dissolution of the calculus upon formation of the electrolytic circuit of the pair of electrodes.

BRIEF DESCRIPTION OF THE DRAWINGS

The particular technical characteristics and advantages of the invention will become apparent from the following detailed description of some preferred but not exclusive embodiments of the device according to the invention, illustrated only by way of non-limitative example in the accompanying drawings, wherein:

FIG. 1 is a partial perspective view of a sleeve for insertion in the urinary cavity, used in the device according to the present invention;

FIG. 2 is a perspective view of an embodiment of the device according to the present invention;

FIG. 3 is a perspective view of a probe which contains a metal filament which constitutes the anode of the device according to the present invention;

FIG. 4 is a perspective view of a first embodiment of an additional probe which can be inserted in the device according to the invention shown in FIG. 1;

FIG. 5 is a perspective view of a second embodiment of the additional probe which can be inserted in the device according to the invention shown in FIG. 1;

FIG. 6 is a perspective view of a third embodiment of the additional probe which can be inserted in the device according to the present invention shown in FIG. 1;

FIG. 6a is a perspective view of a fourth embodiment of the additional probe which can be inserted in the device according to the present invention;

FIG. 7 is a perspective view of a vest which can be used in association with the device according to the invention;

FIG. 8 is a perspective view of a variation of the embodiment of the device according to the invention shown in FIG. 3–6a;

FIG. 9 is a detail view of elastic means which are arranged at one end of the sleeve of the device according to the present invention;

DESCRIPTION OF THE PREFERRED EMBODIMENTS

Figure 10:
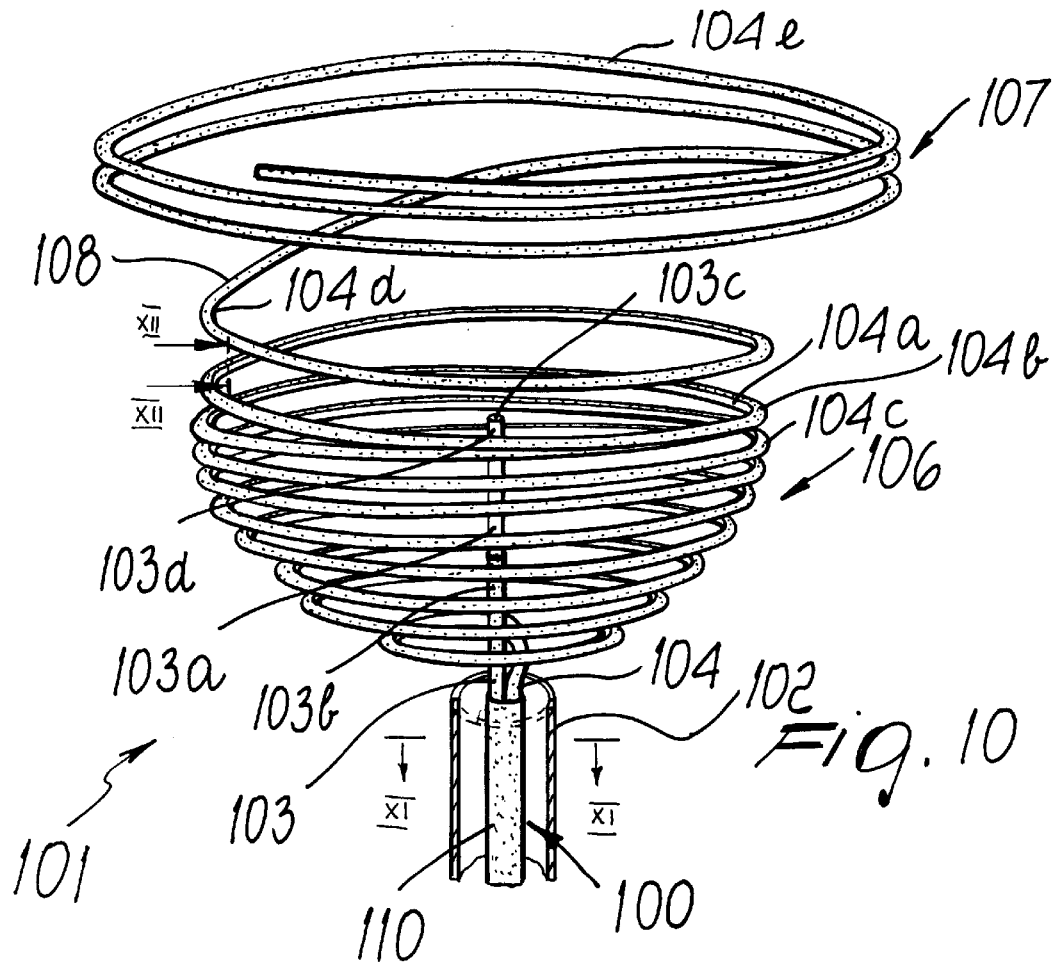
FIG. 10 is a partial sectional view of another embodiment of the device for the dissolution of urinary calculi according to the invention.

With reference to the above figures, the device according to the present invention, generally designated by the reference numeral 1, comprises a tubular outer sleeve 2, which is meant to be inserted in the urinary cavities of a patient with urinary calculosis, and at least one probe 3, which can be accommodated in the sleeve 2 and can slide therein.

The probe 3 in turn accommodates a filament made of conducting material 4, which can slide therein and is meant to make contact with a calculus which is present within the urinary cavities of the patient.

The filament of conducting material 4 constitutes an anode electrode of the device according to the invention.

The sleeve 2 furthermore accommodates a cathode electrode 5 for forming, together with the anode electrode 4, an electrolytic circuit meant to dissolve the calculus.

The metal filament 4 protrudes, in the active condition, from the probe 3 that accommodates it, so as to assume a basket-like configuration which is meant to trap and retain the calculus to be dissolved.

The basket is constituted by an insulating sheath 6 inside which a plurality of conducting filaments 7 are embedded; said filaments are substantially parallel to the axis of the sleeve 2 and are connected to a transverse wire 8 which is arranged substantially at right angles to them.

The wire 8 delimits the region of the basket in which the conducting filaments 7 are present from the region in which only the insulating sheath 6 is present.

Said sheath is provided with microperforations which allow gasses to escape from the sheath and with micropoints 9 which protrude from the sheath and make contact with the calculus which is trapped inside the basket and is retained between the basket and the end of the sleeve 2.

The conducting filament 4 accommodated within the probe 3 opens out when said filament is made to slide out of the probe 3.

It is also possible to provide an additional anode electrode besides the anode electrode 4.

Said additional anode electrode, constituted by an additional conducting filament 10, is slidingly accommodated within an additional probe 11 which is contained in the sleeve 2 like the probe 3.

The filament 10, in protruding from the probe 11, opens out and assumes configurations such as those shown in FIGS. 4–6.

Thus, for example, the conducting filament 10 can maintain the simple pointed configuration of FIG. 6a or can assume the multiple-point configuration of FIG. 4, or the spherical configuration of FIG. 5 or the conical configuration of FIG. 6.

These configurations are provided merely by way of example and other embodiments may be devised without altering the inventive concept on which the present invention is based.

The end of the sleeve 2 which lies opposite to the end inserted in the urinary cavities is coupled to a plate 12. Elastic means are advantageously interposed at the proximal end of the sleeve, between said sleeve and the proximal end of the probe that has trapped the calculus; said means are constituted by a spring 18, as shown in FIG. 9.

The plate 12 is supported by a belt 13 of a vest 14 which is worn by the patient during treatment.

A power source, such as for example a battery 15, supplies the anode electrode 4 and the cathode electrode 5 to provide an electrolytic circuit. Moreover, the power source may be supplied with a computerized system capable of inverting the polarity of said circuit.

In practice it has been observed that the device and the treatment method according to the invention fully achieve the intended aim and objects, since they allow effective dissolution of even large urinary calculi without having to resort to general anaesthesia of the patient.

The device thus conceived is susceptible of numerous modifications and variations, all of which are within the scope of the inventive concept.

Thus, for example, it is possible to provide for the presence of the anode electrode 10 alone instead of the anode electrode 4 or for the presence of the anode electrodes 4 and 10 in combination.

FIG. 8 is a view of another embodiment of the probe with expandable tip which can be inserted in the tubular sleeve 2. In this case, the conducting filament 4 provided inside the probe 3 is meant to expand, when it protrudes from the probe, like a parachute in order to trap and retain a calculus.

The portion of the filament 4 which is parachute-shaped is constituted by a thin platinum mesh 16 which is externally covered by a perforated sheath 17 made of insulating material.

All the details may furthermore be replaced with other technically equivalent elements.

In practice, the materials employed, so long as they are compatible with the specific use, as well as the dimensions, may be any according to requirements and to the state of the art.

According to another aspect, the present invention provides for a method for treating urinary calculi by intracavitary electrolitholysis, which comprises:

the insertion of a tubular sleeve in a urinary cavity of a patient requiring treatment, placing an end of said tubular sleeve proximate to a urinary calculus;

positioning a cathode electrode and an anode electrode inside said tubular sleeve;

sliding said anode electrode along said sleeve, so as to make an electrically conducting tip protrude in an active position in which it is in contact with the urinary calculus;

electrically connecting said cathode electrode and said anode electrode to an external power source;

applying a difference in potential across said electrodes so as to produce a flow of electric current which is suitable to produce electrolitholysis of the urinary calculus.

According to a preferred embodiment of the method according to the invention, the anode electrode is constituted by a filament made of conducting material which is accommodated within a probe made of insulating material, and said filament has, at a portion (distal end) which is meant to protrude from the sleeve, an expandable basket-like configuration for trapping and retaining said calculus. According to this embodiment, the calculus is trapped in the basket of the anode and subjected to electrolysis for a period of time which is sufficient to cause its complete dissolution. In order to reduce the electrolitholysis time, an additional anode electrode is advantageously inserted through the internal passage of the sleeve and then placed in direct contact with the trapped urinary calculus. Said additional anode electrode is advantageously constituted by an additional probe made of insulating material, which accommodates a conducting filament provided with an expandable tip (distal end) which is meant to make contact with the previously trapped calculus.

The preliminary steps of the method according to the invention, which include the insertion of the sleeve and of the probes, follow the timings and methods of percutaneous access to the kidney or, as an alternative, follow access pathways along the urinary tract, which include the insertion of the tubular sheath and of the probes along the urethra, bladder and ureter, until the location of the urinary calculus is reached.

The treatment method according to the invention can be advantageously provided as an outpatient treatment or by admission to a day hospital.

According to a particularly preferred embodiment of the method for the electrolytic dissolution of urinary calculi according to the invention, the following steps are performed.

The patient requiring treatment is placed in prone position on a bed, for example of the radiological type, and the region of the skin where the percutaneous access pathway is provided is disinfected.

Then an anaesthetic is infiltrated locally and a puncture is performed with a thin and long needle, such as a Chiba needle, with a direction and angle which reach the calculus, which is located for example by fluoroscopic examination. Once the renal cavity has been entered, a contrast medium is advantageously infused in order to visualize the cavities during the execution of the method. The kidney is then punctured with a larger-diameter needle, and once the cavity has been entered, a flexible metal guide, of the type commonly used in nephrostomy operations, is inserted through said larger needle until its soft and flexible end is sufficiently coiled along the walls of the renal pelvis or has descended into the ureter. At this point, while keeping the guide in place, the needle is extracted over it and dilators of gradually larger diameters are inserted in succession along the guide, entering the cavity and extracting them after a short retention period. Once the last dilator has been inserted, the tubular sleeve of the device according to the invention is made to advance thereon until it enters the renal cavity. The dilator is then extracted and the calculus is captured, preferably under fluoroscopic control, by introducing an anode electrode which advantageously has, at its active end, an expandable basket-like shape which is accommodated within a probe of the above-described type. During the initial steps of the treatment method, the basket-shaped end of the anode electrode is kept inside the probe.

At this point, the anode electrode is made to slide along the probe, making the basket exit proximate to the calculus, so as to trap it inside the basket.

In this step, the electrode passes from an inactive position to the active position, in which it is preferably ogive- or basket-shaped so that it can trap and retain the calculus during dissolution.

Once the calculus has been trapped in the basket, it is pulled towards the sleeve (towards the outside of the patient's body) so as to lock it in a constriction position, with respect to the tubular sleeve, from which it cannot disengage easily. The end of the anode electrode which is opposite to the one inserted in the body is rigidly coupled, according to a preferred embodiment of the method according to the invention, to a spring which acts by pulling the electrode outward with respect to the body, allowing the conducting parts of the basket to remain constantly in close contact with the calculus. The anode electrode and a cathode electrode, arranged beforehand in the tubular sleeve, are then connected to a power source which provides an electric power differential which allows electrolytic dissolution of the calculus without damaging the surrounding tissues. Advantageously, the applied electric current has a voltage between 6 and 20 volts and an intensity between 5 and 80 mA.

According to another embodiment of the treatment method according to the invention, an additional anode electrode is inserted along the tubular sleeve; said anode electrode is constituted by an additional probe which accommodates a filament made of conducting material and provided with an extractable tip. The probe is arranged so that its extractable tip is in direct contact with the calculus in order to increase the electrolitholysis effect.

Said additional anode electrode can have, proximate to its tip (distal end) inserted in the patient's body, any of the above-described configurations, selected appropriately according to the size of the calculus to be dissolved.

When the electric circuit is closed, a flow of electrons is produced and conveyed towards the calculus to be dissolved.

The conducting end of the anode electrodes, placed in contact with the calculus, concentrates the flow of electric current. During the initial steps of the electrolitholysis process, a hole is formed in the calculus and becomes larger over time. As the hole enlarges, the end of the electrode protrudes from the probe and enters the calculus. When an anode electrode provided with a plurality of points is used, alone or in addition to further anode electrodes, the electrolitholysis effect is particularly conspicuous and the treatment times are reduced considerably.

The flow of current that dissolves the calculus is ensured by the urinary environment, which is constituted by a solution (urine) which is particularly rich in ions (electrolytic solution). The flow of current is limited to the inside of the sheath-sleeve system of the device according to the invention.

It has been observed that during the execution of intracavitary electrolysis the organic material which is present in the urine, constituted by protein, mucus and particles of various origin, tends to migrate towards the end of the anode electrode in the form of a dense yellowish suspension without however interfering with electrolysis.

It has furthermore been observed that urine becomes increasingly foamy as electrolysis continues, owing to the presence of gases (oxygen and chlorine) which form proximate to the tips of the electrodes.

These effects, however, do not hinder the execution of the treatment method, since the urine, which is produced continuously, is conveyed along the urinary tract, removing the impurities contained therein.

It has been observed that the treatment method according to the invention can entail dissolution times between 2 hours and 7 days yet it does not interfere with urinary filtration and with its progress along the urinary tract. A high production of urine furthermore facilitates the development of the intracavitary electrolitholysis which is the basis of the present invention, since the electrolytic solution is changed continuously and is richer in salts and less loaded with organic materials and foam.

During the execution of the treatment method according to the invention, the means inserted in the urinary cavity can be connected to an external device of the type described above, which is suitable to keep the probes and the electrodes in an intracavitary position.

This external device comprises a spring which is suitable to keep the anode electrode against the calculus with a constant pressure; the spring is preferably placed against a plate which is arranged at the exit point of the probes, for example proximate to the lumbar region of the patient. The plate is advantageously connected to a belt or vest of the type described above, which can be conveniently provided with a power source.

In a preferred embodiment of the invention, the plate is arranged on the belt at the point where the intrarenal probes emerge from the patient's hip, advantageously proximate to an area which is arranged at 2 to 3 centimeters from the iliac crest along the posterior axillary line. The plate performs various functions, including that of keeping the probes locked, protecting them against external stresses, of allowing and protecting the electric contacts between the power source and the probes, and of applying a spring-loaded thrust to any additional electrodes so as to maintain constant contact with the calculus. This device allows the patient, after the initial nephrostorny operations, to conduct a normal life while the electrolytic process continues the dissolution action.

The treated patient must keep the plate in position during the night, for example by assuming a prone position or by lying on the contralateral side with respect to the affected one when resting.

It has been found that the treatment method according to the invention allows dissolution of a urinary calculus weighing approximately 500 mg over a period between 3 and 70 hours, according to the type of material that constitutes the calculus.

In particular, the electrolytic method according to the invention dissolves calcium phosphate calculi in 2–8 hours, with a dissolution rate of approximately 150 mg/hour; dissolves uric acid calculi at a rate of approximately 11 mg/hour; and dissolves calculi of calcium oxalate, cystine and mixtures thereof at a rate of approximately 7 mg/hour.

The following examples are provided merely by way of description of the electrolytic dissolution method according to the present invention and must not be understood as limiting the scope of the invention as defined by the appended claims.

EXAMPLE 1

Chemically-synthesized substances were subjected to the electrolitholysis process according to the invention instead of natural calculi, since calculi contain organic material which alters the degree of crystallinity of the solid and accordingly alters the dissolution process. The chemical substances used were in the form of highly compressed tablets which had a reproducible behavior.

A calcium oxalate tablet was suspended in an electrolytic cell by passing a platinum wire with a diameter of 0.7 mm through a narrow hole formed therein: the wire was connected to the positive pole of a constant-current source and the circuit was completed by a platinum leaf cathode and by an electrolytic solution of 0.3M sodium chloride.

Several experiments were conducted, using current strengths between 10 and 100 mA: the hole, with the platinum wire inserted through it, invariably became gradually larger until the tablet fell in fragments, losing contact with the anode. The residual fragments of the tablet, after being washed, dried and weighed, indicated that a substantial part of the solid had been dissolved.

However, it was difficult to say whether dissolution had occurred by direct anodic oxidation of the calcium oxalate or by means of an indirect oxidation caused by the nascent oxygen produced at the anode or by means of a protolysis of the oxalate ion or by means of the cooperation of these various dissolution mechanisms.

On the basis of thermodynamic and kinetic considerations, we can infer that dissolution occurs predominantly by indirect oxidation on the part of the nascent oxygen and partly by direct oxidation.

In all the tests, the pH of the solution never rose above neutrality, confirming the indication that chlorine development at the anode is not significant.

EXAMPLE 2

As in Example 1, calcium phosphate tablets were prepared; the relation is thermodynamically favored and therefore very fast, much faster than that of calcium oxalate. In this case too, the pH of the solution did not change appreciably.

The reproducibility of the composition and of the compactness of the oxalate and calcium phosphate tablets allows to correlate the efficiency of the current, and accordingly the dissolution rate, with other parameters which can affect the electrolytic process. No particular variations were noted by replacing the 0.3M solution of sodium chloride with a so-called synthetic urine, i.e., a solution that contains the main solutes of natural urine. Increasing the strength of the current did not produce greater dissolution of the solid. However, an appreciable increase in the dissolution rate was observed when increasing the density of the current by decreasing the contact surface of the anode with the solid, thus converting the anode into a polarizable electrode.

EXAMPLE 3

Natural calculi removed from patients affected by urinary calculosis were subjected to the electrolytic dissolution process: the calculus, wrapped in a platinum mesh connected to the anode and insulated electrically from the solution, was placed into contact with a platinum point, also connected to the anode, which was constantly pushed against it by a metal spring. The electrolytic solution was constituted by synthetic urine, as described above.

At least ten calculi of each kind of the four compositions (oxalate, phosphate, uric acid and cystine) of different weight, density, shape etcetera were subjected to anodic dissolution. Current strengths up to 150 mA were applied. In all cases, the platinum point perforated the calculus from end to end at different rates: higher ones for phosphate and uric acid and lower ones for oxalate and cystine.

By observing the corrosion on the surfaces of the calculus during electrolysis, it was noted that the platinum mesh performed a much less effective lysis than the point.

Experimental results as a whole demonstrate that calcium phosphate calculi are surprisingly dissolved in a few hours at a rate of approximately 150 mg/hour; uric acid calculi are dissolved much more slowly, at a rate of approximately 11 mg/hour; calcium oxalate and cystine calculi are dissolved at a rate of approximately 7 mg/hour FIG. 10 illustrates another preferred embodiment of a device 101 for the dissolution of urinary calculi adapted to be used in a similar manner as the previously described embodiments of the invention.

Device 101 includes a filament 100 (main filament) including two or more sub-filaments (electrodes 103 and 104) connected to a source of electricity so as to form an electrolytic circuit for electrolytic calculus dissolution and a tubular sleeve 102 for the insertion of said filament in a urinary cavity of a patient. In a manner similar to the previously described embodiments of the invention, the main filament 100 is slidably accommodated inside tubular sleeve 102 between a first position in which the slidable filament is substantially completely accommodated inside tubular sleeve 102 for facilitating the insertion of the filament 100 inside the urinary cavity of the patient, and a second position in which the slidable filament 100 protrudes outside of tubular sleeve 102 once it has been inserted inside the urinary cavity of the patient for making contact with a calculus located in the urinary cavity of the patient for electrolytic dissolution of the calculus upon formation of the electrolytic circuit.

As seen in FIG. 10, device 101 has two electrodes 103, 104 (sub-filaments): a first electrode 103 and a second peripheral spiral shaped electrode 104 which extends about first electrode 103 in a spiral-like fashion. First and second electrodes 103 and 104 are both slidably accommodated inside tubular sleeve 102. In particular, second electrode 104 is slidably accommodated inside tubular sleeve 102 between a first position, in which second electrode 104 is substantially completely accommodated inside tubular sleeve 102 for facilitating the insertion of the device 101 inside the urinary cavity of the patient, and a second position as shown in FIG. 10 in which second electrode 104 protrudes outside of tubular sleeve 102 once it has been inserted inside the urinary cavity of the patient for making contact with a calculus located in the urinary cavity of the patient for electrolytic dissolution of the calculus upon formation of the electrolytic circuit of first and second electrodes 103 and 104. Moreover, first electrode 103 is slidably accommodated inside tubular sleeve 102 between a first position, in which first electrode 103 is substantially completely accommodated inside tubular sleeve 102 for facilitating the insertion of the device 101 inside the urinary cavity of the patient, and a second position as shown in FIG. 10 in which first electrode 103 protrudes outside of tubular sleeve 102 once it has been inserted inside the urinary cavity of the patient for facilitating the formation of the electrolytic circuit between first electrode 103 arranged in its respective second position protruding from tubular sleeve 102 and second electrode 104 arranged in its respective second position protruding from tubular sleeve 102 and in contact with a calculus located in the urinary cavity of the patient for electrolytic dissolution of the calculus upon formation of the electrolytic circuit of first and second electrodes 103 and 104.

Figure 11:
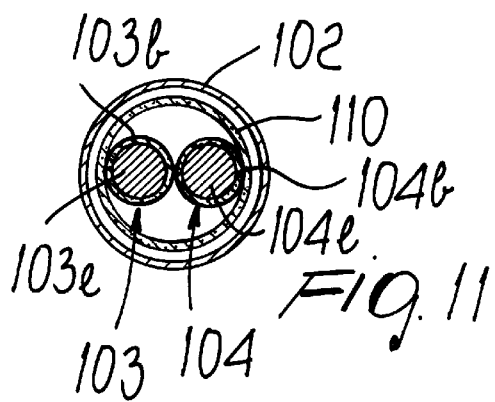
FIG. 11 is a sectional view taken along the plane XI—XI of FIG. 10.

In the preferred embodiment as seen in FIGS. 10 and 11, both first and second electrodes 103 and 104 are fixed inside a flexible sheath 110 which may also be made of electrically insulating material, such that both electrodes 103 and 104 are moved simultaneously together between their first and second positions described above.

FIG. 10 shows both first and second electrodes 103 and 104 in their respective second positions as described above, and both first and second electrodes 103 and 104 are slidable downwardly into tubular sleeve 102 with respect to drawing FIG. 10 into their respective first positions as described above, in which both first and second electrodes 103 and 104 are substantially completely accommodated inside tubular sleeve 102, and in which second electrode 104 is compressed into tubular sleeve 102 substantially about the central axis of tubular sleeve 102. Thus from the radially expanded second position of FIG. 10 of second electrode 104, the outer portions of second electrode 104 are inwardly compressed and folded upwardly (with respect to FIG. 10) as second electrode 104 is slid into tubular sleeve 102 so as to form an axially elongated configuration in the first position of second electrode 104. For this purpose, second electrode 104 is formed of flexible material which in an unflexed state assumes the configuration of the second position as seen in FIG. 10.

First electrode 103 comprises a filament 103a made of electrically conducting material, and a probe sheath 103b made of electrically insulating material inside which filament 103a is accommodated. Filament 103a may be fixedly accommodated inside sheath 103b such that the tip 103c of filament 103a is always exposed outside of the top edge 103d of probe sheath 103b, or alternatively filament 103a may be slidably accommodated inside sheath 103b such that tip 103c is selectively exposed outside of top sheath edge 103d (for example once first electrode 103 has been arranged in its respective second position) or such that tip 103c is substantially completely accommodated inside sheath 103b (for example when first electrode 103 is arranged in its respective first position).

Figure 12:
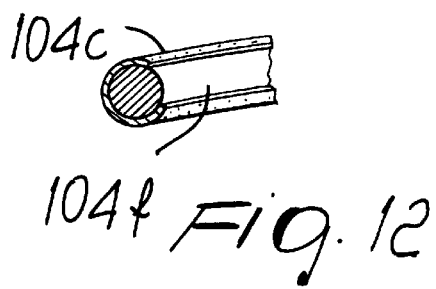
FIG. 12 is a detail sectional view of the device of FIG. 10.

Second electrode 104 is spiral shaped about the central longitudinal axis of device 101 and comprises a lower conical spiral portion 106, an upper peripheral ring portion 107, and an intermediate connecting portion 108 which connects lower conical spiral portion 106 and upper portion 107. Second electrode 104 comprises a filament 104a made of electrically conducting material, and in the preferred embodiment shown in FIG. 10, a first insulating sheath portion 104b covering the portion of filament 104a which is positioned inside tubular sleeve 102, a second insulating sheath portion 104c covering the portion of filament 104a which is positioned at lower conical spiral portion 106, a third insulating sheath portion 104d covering the portion of filament 104a which is positioned at connecting portion 108, and a fourth insulating sheath portion 104e covering the portion of filament 104a of second electrode 104 which is arranged at upper portion 107. Insulating sheath portions 104b, 104d, and 104e preferably completely cover and electrically insulate their respective portions of filament 104a, while insulating sheath portion 104c only partially covers filament 104a, as seen in FIG. 12, such that an inwardly facing portion 104f of filament 104a is arranged at lower conical spiral portion 106. Portion 104f faces inwardly of the lower conical spiral portion 106 such that it is thus an exposed electrically conducting material portion arranged for direct contact with a calculus located in the urinary cavity of the patient for electrolytic dissolution of the calculus upon formation of the electrolytic circuit between first and second electrodes 103 and 104.

Since probe sheath 103b provides adequate electrical insulation between filament 103a and filament 104a of second electrode 104 to avoid any electrical short circuits occurring due to contact between filament 103a and filament 104a, it is possible to do without any one or more of insulating sheath portions 104b, 104c, 104d and 104e.

Figure 13:
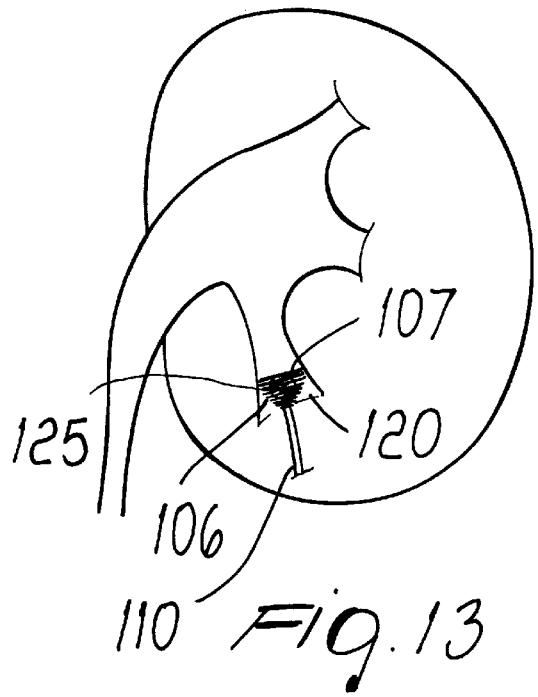
FIG. 13 is a diagrammatic view of the device of FIG. 10 positioned in the outlet of a patient's renal calyx.

As seen in FIG. 13, upper ring portion 107 may have a diameter bigger than the diameter of the ring-shaped edge of the outlet 120 of a patient's renal calyx, such that in operation of device 101, upper ring portion 107 may be arranged in direct contact with such ring-shaped edge of the outlet 120 of a patient's renal calyx for slightly divaricating such ring-shaped edge of the outlet 120 of a patient's renal calyx, for facilitating the engagement of a calculus located at the renal calyx outlet in the expanded end of second electrode 104, and particularly for facilitating contact of exposed portion 104f with such calculus. Insulating sheath portion 104e arranged at upper ring portion 107 is particularly useful in this event for avoiding discomfort to the patient. It has also been envisaged that only the upwardly facing (in FIG. 10) part of upper ring portion 107 is provided with electrical insulation, while the downwardly facing part may be provided as exposed electrically conducting material. According to the preferred embodiment shown, the winding of connecting portion 108 opens up from lower portion 106 for interconnection to upper portion 107, which has a larger radius than lower portion 106 and intermediate connection portion 108. Expanded lower and upper portions 106 and 107 form a kind of basket-shaped container for containing the patient's calculus, which container is delimited on the top by the upper portion 106, on the bottom by lower portion 106, and laterally by a tronco-conical surface geometrically extending between the peripheries of lower and upper portions 106 and 107. In the embodiment of FIG. 10, the entire portion of filament tip 103c is electrically exposed. It has been envisaged that other configurations of first electrode 103 may be provided, which preferably have an electrically exposed portion arranged in any position inside the basket-shaped container formed by lower and upper portions 106 and 107 for facilitating the formation of the electrolytic circuit between the first and second electrodes arranged in their respective second positions. FIG. 12 further illustrates that once device 101 has been positioned so that upper ring portion 107 is arranged in contact with outlet 120 of a patient's renal calyx and calculus 125 has fallen by gravity to be entrapped inside lower portion 106, tubular sleeve 102 may be fully removed and electrolytic dissolution of calculus 125 may occur upon formation of the electrolytic circuit of first and second electrodes 103 and 104.

What is claimed is:

1. A device for the dissolution of urinary calculi in patients affected by urinary calculosis, comprising:
    a tubular sleeve adapted for insertion in a urinary cavity of a patient; and
    two or more electrodes connectable to a source of electricity so as to form an electrolytic circuit for electrolytic calculus dissolution;
    said two or more electrodes comprising at least one slideable electrode which is slidably accommodated inside said tubular sleeve between:
        a first position in which said at least one slideable electrode is substantially completely accommodated inside said tubular sleeve for facilitating the insertion of the tubular sleeve inside the urinary cavity of the patient; and
        a second position in which said at least one slideable electrode protrudes outside of said tubular sleeve once said tubular sleeve has been inserted inside the urinary cavity of the patient for making contact with a calculus located in the urinary cavity of the patient for electrolytic dissolution of the calculus upon formation of said electrolytic circuit of said two or more electrodes.

2. The device of claim 1 wherein said at least one slideable electrode slidably accommodated inside said tubular sleeve between said first and second positions comprises a probe and a filament of electrically conducting material internally accommodated within said probe, said probe being slidably accommodated inside said tubular sleeve between said first and second positions, and said filament having an end portion for protruding from said probe for making contact with the calculus located in the urinary cavity of the patient.

3. The device of claim 2 wherein said filament is slidably accommodated inside said probe between an inactive position in which said end portion of said filament is substantially completely accommodated within said probe and an active position in which said end portion of said filament protrudes from said tubular sleeve for making contact with the calculus located in the urinary cavity of the patient.

4. The device of claim 3 wherein said end portion of said filament is expanded in said active position with respect to said inactive position.

5. The device of claim 4 wherein said end portion of said filament is shaped in said active position for trapping the calculus between said filament and the end of said tubular sleeve from which said end portion of said filament protrudes.

6. The device of claim 1 wherein a fixed electrode of said two or more electrodes other than said at least one slideable electrode slidably accommodated inside said tubular sleeve is fixed in position inside said tubular sleeve.

7. The device of claim 6 comprising a first slideable electrode and a second slideable electrode each slidably accommodated inside said tubular sleeve between respective said first and second positions and each comprising a respective probe and a respective filament of electrically conducting material internally slidably accommodated within said respective probe which is slidably accommodated inside said tubular sleeve between said respective first and second positions, and said filament of said second slideable electrode having a respective expandable end portion for protruding from said probe of said second slideable electrode in an active position in which said expandable end portion of said filament of said second slideble electrode protrudes from said probe for making contact with the calculus located in the urinary cavity of the patient while in an inactive position said expandable end portion of said filament of said second slideable electrode is substantially completely accommodated within said probe of said second slideable electrode.

8. The device of claim 7 wherein for said first slideable electrode slidably accommodated inside said tubular sleeve, said end portion of said filament is shaped in said active position for trapping the calculus between said filament and the end of said tubular sleeve from which said end portion of said filament protrudes, and wherein for said second slideable electrode said expandable end portion has a plurality of expanded points for making contact with the calculus in said active position of said second slideable electrode.

9. The device of claim 8 wherein said second slideable electrode is pushed continuously against the calculus by an elastic means.

10. The device of claim 1 comprising two slideable electrodes each of which is slidably accommodated inside said tubular sleeve.

11. The device of claim 10, wherein a first one of said two slideable electrodes is a linear electrode, and a second one of said two slideable electrodes is a spiral shaped electrode which extends about said linear electrode and which is slidably accommodated inside said tubular sleeve between said first and second positions.

12. The device of claim 11, wherein said linear electrode is slidably accommodated inside said tubular sleeve between a first position, in which said linear electrode is substantially completely accommodated inside said tubular sleeve for facilitating the insertion of said electrode inside the urinary cavity of the patient, and a second position, in which said linear electrode protrudes outside of said tubular sleeve for facilitating the formation of said electrolytic circuit between said linear electrode arranged in its respective second position and said spiral shaped electrode arranged in its respective second position.

13. The device of claim 12, wherein said spiral-shaped electrode comprises a lower conical spiral portion arranged adjacent the end of said tubular sleeve when said spiral-shaped electrode is arranged in its respective second position, an upper peripheral ring portion arranged distally from said lower conical spiral portion, and a connecting portion interconnecting said lower conical spiral portion and said upper ring portion, said lower conical spiral portion having an exposed electrically conducting portion for contact with the patient's calculus.

14. The device of claim 13, wherein said lower conical spiral portion and said upper peripheral ring portion of said spiral-shaped electrode form an expanded basket-shaped container for containing a patient's calculus when said spiral-shaped electrode is arranged in its respective second position.

15. The device of claim 13, wherein said upper ring portion is electrically insulated.

16. A method for treating urinary calculoses by intracavitary electrolitholysis, comprising the steps of:

inserting a tubular sleeve in a urinary cavity of a patient so as to position a tip of said tubular sleeve proximate to a urinary calculus of the patient;

positioning two or more electrodes inside said tubular sleeve;

sliding said electrodes along said sleeve so as to cause the protrusion of an electrically conducting tip of said electrodes from said tubular sleeve in an active position in which said electrodes are in contact with the urinary calculus of the patient;

electrically connecting said electrodes to an external power source;

applying a potential difference across said electrodes in order to create a flow of electric current which is suitable to produce electrolitholysis of the urinary calculus.

17. A method according to claim 16, including: sliding at least one of said electrodes formed by a filament made of electrically conducting material and having said electrically conducting tip which is slidably accommodated within a probe; and sliding said filament inside said probe such that said electrically conducting tip expands outside of said probe and makes contact with the urinary calculus of the patient.

18. A method according to claim 17, including retaining the urinary calculus by means of the electrically conducting tip of said filament which has expanded.

19. A method according to claim 16, further comprising the steps of:

slidably inserting in said sleeve a further electrode comprising a probe which accommodates a filament made of electrically conducting material which has an extractable tip;

placing said extractable tip of said further electrode in contact with the urinary calculus and keeping it in contact with said calculus substantially throughout the treatment; and applying an electric current in order to increase electrolitholysis of the calculus.

20. A method according to claim 16, further including the withdrawal of said tubular sleeve after positioning said electrodes in active position in contact with urinary calculation of the patient.

21. A method according to claim 16, including inserting said tubular sleeve in the urinary cavity percutaneously.

22. A method according to claim 16, including inserting said tubular sleeve in the urinary cavity through the urinary tract.

* * * * *